United States Patent [19]

Sikora

[11] Patent Number: 4,983,729

[45] Date of Patent: Jan. 8, 1991

[54] DNA FRAGMENT ENCODING A RUBBER POLYMERASE AND ITS USE

[75] Inventor: Leonard A. Sikora, Stow, Ohio

[73] Assignee: The Goodyear Tire & Rubber Company, Akron, Ohio

[21] Appl. No.: 424,138

[22] Filed: Oct. 19, 1989

[51] Int. Cl.$^5$ .................... C07H 15/12; C07H 19/06; C12N 1/20; C12N 15/00
[52] U.S. Cl. ........................................ 536/28; 536/26; 536/27; 435/252.3; 435/252.31; 435/252.33; 435/320
[58] Field of Search ................. 536/27, 28; 435/252.3, 435/252.31, 252.33, 320, 199, 166, 167; 530/300

[56] References Cited

U.S. PATENT DOCUMENTS

| | | | |
|---|---|---|---|
| 4,338,399 | 7/1982 | Weil et al. | 435/167 |
| 4,638,028 | 1/1987 | Lui et al. | 435/166 |
| 4,698,304 | 10/1987 | Fukuda et al. | 435/167 |
| 4,863,862 | 9/1989 | Fukuda et al. | 435/166 |

OTHER PUBLICATIONS

13 Encyclopedia of Polymer Science and Engineering, 687–716, 2nd ed., John Wiley & Sons, Inc., 1988.
Rubber Developments 34:96–98, 1981.
Biomass Digest, p. 8, Dec. 1984.
Bioprocessing Technology, p. 10, Dec. 1986.
Technol. Forecasts and Technol. Surveys, pp. 13–14, Oct. 1987.
Bioprocessing Technology, pp. 7 & 12, Nov. 1988.

*Primary Examiner*—Robert A. Wax
*Assistant Examiner*—Stephanie W. Zitomer
*Attorney, Agent, or Firm*—Finnegan, Henderson, Farabow, Garrett & Dunner

[57] ABSTRACT

A DNA fragment containing a DNA sequence that encodes rubber polymerase or a fragment thereof is provided, as well as a hybrid vector and a transformed host each containing the DNA fragment. The present invention also provides for a process for the production of rubber in vitro and in vivo by transferring the DNA fragment to a host and culturing the transformed host in an environment that is suitable for the production of rubber.

27 Claims, 1 Drawing Sheet

A RESTRICTION MAP OF THE HEVEA RUBBER POLYMERASE GENE SHOWING THE LOCATION OF THE ENZYMES WHICH DIGEST THIS DNA. THE RUBBER POLYMERASE GENE IS 1900 BASE PAIRS IN LENGTH. THE SIZE OF THE VARIOUS RESTRICTION FRAGMENTS IS SHOWN IN THE BRACKETS.

DNA FRAGMENT ENCODING A RUBBER POLYMERASE AND ITS USE

BACKGROUND OF THE INVENTION

The present invention relates to a DNA fragment that is cap encoding rubber polymerase, also known as rubber transferase, and to a hybrid vector and a transformed host, each comprising the DNA fragment The present invention also relates to a process of producing rubber in vitro and a process of producing rubber in vivo.

According to 13 ENCYCLOPEDIA OF POLYMER SCIENCE AND ENGINEERING 687, 2nd ed., John Wiley & Sons, Inc., (1988), natural rubber, cis-1,4-polyisoprene, is produced naturally in over 200 species of plants Two of these plants, *Hevea brasiliensis* and *Parthenium argentatum* ("guayule") produce sufficiently high molecular weight rubber to be utilized for commercial production of natural rubber.

Efforts have been made to increase the production of rubber in rubber-producing plants by selection and breeding of improved planting material or better methods of tapping and general husbandry, or by chemically stimulating the yield. Despite such efforts, however, the amount of rubber such plants can produce or can be stimulated to produce, is limited by the rate of rubber synthesis by the plant.

The biochemical pathway leading to the production of rubber has been studied and is believed to involve at least 17 steps starting from simple sugars, each step being mediated by an enzyme. Rubber Developments, 34: 96-98 1981. One enzyme, rubber polymerase, has been substantially purified and is believed to mediate the polymerization of isopentenyl pyrophosphate ("IPP") onto an allylic pyrophosphate to produce rubber, as described in U.S. Pat. No. 4,638,028, the contents of which are incorporated herein by reference.

SUMMARY OF THE INVENTION

It is therefore, an object of the present invention to provide a method for increasing the production of rubber It is another object of the present invention to provide a method for increasing the production of rubber in vitro or in vivo.

It is still another object of the present invention to isolate the DNA fragment that encodes rubber polymerase.

It is as yet another object of the present invention to provide a hybrid vector containing the above-mentioned DNA fragment.

It is further object of the present invention to provide a transformed host that contains the DNA fragment or the hybrid vector and is capable of expressing the DNA fragment.

In accomplishing these and other objects and advantages, there has been provided a DNA fragment that comprises a first DNA sequence that encodes rubber polymerase or a fragment thereof.

In accordance with another aspect of the present invention, there has been provided a DNA fragment as above, the fragment further comprising a second DNA sequence that is capable of influencing the expression of the first DNA sequence.

In accordance with yet another object of the present invention, there has been provided a DNA fragment as above, the first DNA sequence of which is capable of encoding an N-terminal amino acid sequence leu-thr-gln-gly-lys-lys-ile-thr-val-leu-ser-ile-asp-gly-gly.

In accordance with yet another object of the present invention, there has been provided a DNA fragment as above, the first DNA sequence of which is capable of encoding an amino acid sequence.

val—asp—phe—his—leu—ser—ala—leu—phe—lys—ser—leu—

—asp—cys—glu—asp—tyr—tyr—leu—arg—ile.

In accordance with yet another object of the present invention, there has been provided a DNA fragment as above, the first DNA sequence of which is capable of encoding an amino acid sequence tyr—glu—ala—lys—asp—ile—lys—asp—phe—tyr—leu—glu—

—asn—cys—pro—lys—ile—phe—pro—lys—glu—X—arg—asp—

—asn—tyr—X—X—ile,

X being an amino acid.

In accordance with a further object of the present invention, there has been provided a hybrid vector comprising a DNA fragment as above, said vector being capable of being transferred to and replicating in a host.

In accordance with yet a further object of the present invention, there has been provided a hybrid vector as above, said vector being plasmid pRPc1.

In accordance with still another object of the present invention, there has been provided a transformed host comprising the hybrid vector as above, said host being capable of expressing the DNA fragment.

In accordance with another object of the present invention, there has been provided a transformed host comprising the DNA fragment as above, said host being capable of expressing the DNA fragment.

In accordance with another object of the present invention, there has been provided a process for the production of rubber in vitro comprising the steps of providing a DNA fragment as above, transferring said DNA fragment to a host cell to produce a transformed host cell and culturing said transformed host in a suitable medium for the production of rubber polymerase. The rubber polymerase is then used to produce natural rubber in vitro, e.g., as described in U.S. Pat. No. 4,638,028.

In accordance with still another object of the present invention, there has been provided a process for the production of rubber in vivo comprising the steps of providing a DNA fragment as above, transferring said DNA fragment to a host cell to produce a transformed host and culturing said transformed host in an environment that is suitable for the production of rubber in vivo.

Further advantages, objects and features of the present invention will become apparent from the following detailed description. It should be understood, however, that the detailed description, while indicating preferred embodiments of the invention, is given by way of illustration only, since various changes and modifications

DETAILED DESCRIPTION OF THE PREFERRED EMBODIMENTS

Figure 1:
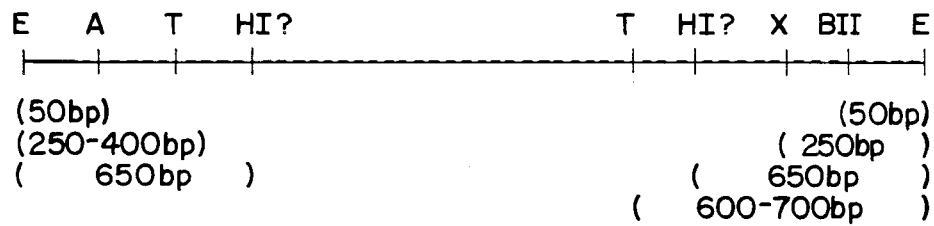
FIG. 1 is a diagram of a restriction map of Hevea rubber polymerase gene, approximately 1900 base pairs in length.

Applicants have isolated a DNA sequence that is capable of encoding a rubber polymerase enzyme (hereafter "rubber polymerase DNA sequence"), and have identified amino acid sequences of fragments of this enzyme Applicants also have identified restriction sites in the rubber polymerase DNA sequence and have provided a hybrid vector and a transformed host, respectively, that contain the rubber polymerase DNA sequence. Moreover, applicants have further provided a method of producing rubber in vitro and in vivo in those plants or other organisms that do not normally produce rubber in any significant amount.

Within the context of the present invention, a "rubber polymerase enzyme" refers to the enzyme that mediates the conversion of IPP to rubber. A "hybrid vector" as used herein, refers to a vector formed by ligation of DNA from a plasmid, bacteriophage, plant virus or other vectors with DNA or cDNA from Hevea or other organisms that are capable of producing rubber polymerase, such plants or other organisms being collectively referred to herein as "plant materials."

In one embodiment of the present invention, plant materials from, e.g., Hevea, are used to produce a cDNA or a DNA library. To produce a DNA library, DNA is extracted from the plant materials and partially digested with a restriction endonuclease to produce a random collection of restricted DNA fragments. Those DNA fragments are inserted into a suitable vector, e.g., bacteriophage lambda, that is capable of carrying a foreign gene and of infecting and replicating in a host cell.

In a preferred embodiment, a cDNA library is constructed that is based upon mRNA sequences isolated from total RNA from the plant materials. A first strand cDNA can be synthesized enzymatically using the isolated mRNA as a template, an oligo dT sequence as a primer and a reverse transcriptase as the enzyme. After construction of the first strand cDNA, a second strand cDNA can be synthesized enzymatically using the first strand cDNA as a template and a DNA polymerase as the enzyme. The resulting double-stranded cDNA molecules are inserted into a suitable vector, to produce a cDNA library.

The resulting cDNA library may be capable of expressing the rubber polymerase gene in *E. coli.* An *E. coli* cell containing the rubber polymerase gene can be identified using antibodies to rubber polymerase or alternatively, using a nucleic acid probe specific for the rubber polymerase gene (hereafter "rubber polymerase gene specific probe"). The rubber polymerase genecontaining cell can then be propagated and large amounts of DNA sequence encoding rubber polymerase can be extracted.

In a preferred embodiment of the present invention, a nucleic acid probe for the identification of rubber polymerase gene is produced in the following manner: Rubber polymerase enzyme is purified by conventional laboratory techniques, e.g., as according to U.S. Pat. No. 4,638,028. The amino acid sequence of at least a portion of the purified rubber polymerase enzyme can be determined and, based upon an identified amino acid sequence, a corresponding nucleotide sequence that is capable of encoding the amino acid sequence can be predicted and a nucleic acid probe can be constructed synthetically based upon the predicted sequence. Because of the degeneracy of the genetic code, however, prediction of the nucleotide sequence on the basis of the amino acid sequence may lead to several possible nucleotide sequences. A collection of different nucleic acid sequences that comprise the various possible nucleotide sequences can be constructed, labeled and used to screen a DNA library containing the rubber polymerase gene.

Plant DNA or DNA from other organisms that hybridizes with a labelled nucleic acid probe specific for the rubber polymerase gene can be identified and isolated The isolated DNA can be ligated to a vector DNA to produce a hybrid vector. The hybrid vector can be used to transform a competent host and to induce the production of rubber polymerase in the host. One such plasmid, pRPcl, constructed from Hevea cDNA and the vector pBR322, and inserted into *E. coli* HB101 has been deposited at the American Type Culture Collection (12301 Parklawn Drive, Rockville, Md. 20852) and has an accession no. 68055.

A vector that is suitable for use in the context of the present invention can be a plasmid or a virus that is capable of being transferred into a host cell or of infecting a host cell and of replicating in a host cell. In a preferred embodiment, a suitable vector is one that is capable of carrying as an insert an entire rubber polymerase DNA sequence in a non-essential region of the vector DNA.

A suitable transformed host is one that is capable of expressing the rubber polymerase DNA sequence. In a preferred embodiment, a suitable transformed host is incapable of producing high molecular. weight rubber in a significant amount before transformation and becomes capable of producing high molecular weight rubber in a significant amount after transformation. Such a host maybe a plant, a bacterium or a fungus. The plant host may be an annual plant such as tobacco species, a grass species or a perennial plant species The bacterium can be any bacterium, e.g., *E. coli,* a Bacillus species or an Agrobacterium species. The fungus is selected from the group consisting of a *lactarius* species and an Aspergillus species.

In the context of the present invention, a "significant amount" in reference to the production of rubber by a plant or other organisms is an amount that is sufficient to justify the economic investment in commercially harvesting rubber from the plant and other organisms concerned or an amount sufficient to justify investment in these sources of rubber as strategic sources of rubber, if necessary.

In another embodiment of the present invention, the DNA fragment that contains the rubber polymerase gene can be ligated to a suitable promoter so as to place the gene under the control of the promoter A suitable promoter is one that is capable of functioning in a transformed host. For example, if the host to be transformed is a plant, the rubber polymerase gene can be ligated to a plant promoter such as Pnos, the promoter for nopaline synthetase; if the host to be transformed is a bacterium, the rubber polymerase gene can be ligated to a bacterial promoter such as the trp or tac promoter of *E. coli*. In the alternative, the rubber polymerase gene can be ligated to a virus promoter such as the 16S and 35S promoter of cauliflower mosaic virus.

In the context of the present invention, a high molecular weight DNA fragment that contains a rubber polymerase gene can be isolated in accordance with any conventional DNA isolation techniques. In one embodiment of the present invention, a method can be employed that is substantially the same as that of Dellaporta et al., *Plant Molecular Biological Reporter*, 4: 19-21 (1983), the contents of which is incorporated herein by reference. In particular, the plant materials are quickly frozen in liquid nitrogen and ground to a fine powder, and the DNA isolated therefrom. As used herein, "plant materials" include all plants and organisms and parts thereof that are capable of producing rubber. The size of the DNA obtained can be analyzed by conventional gel electrophoresis, e g., according to Maniatis et al., MOLECULAR CLONING, Cold Spring Harbor, N.Y. 1982, or to Schlief et al., PRACTICAL METHODS IN MOLECULAR BIOLOGY, Springer-Verlag, Inc., N.Y. 1981, the contents of each of which are incorporated herein by reference.

The DNA isolated from the plant materials can be subjected to partial digestion by restriction endonucleases to obtain a pool of fragments from which structural genes can be cloned employing conventional cloning technology. The restriction enzyme to use depends on the size of the DNA fragments desired.

A suitable vector capable of carrying an entire gene in a non-essential region of its DNA and capable of replicating in a host cell, e.g., a lambda vector, can be ligated to the DNA fragments to generate a library of recombinant DNA molecules. In vitro packaging of these recombinant molecules can yield an infectious phage stock consisting of recombinant clones. The recombinant DNA libraries constructed in this manner can be used for isolation of the rubber polymerase gene and other genes that are important in the biosynthesis of rubber.

In a preferred embodiment of the present invention, a cDNA library, instead of a genomic DNA library, is constructed using mRNA isolated from total RNA. Total RNA is obtained from plant materials by conventional laboratory techniques, e.g. as in Krawetz et al., *Biotechniques*, 2: 542-547, 1984 and Turpen et al., *Biotechniques* 4 11-16, 1986, the contents of which are incorporated herein by reference.

The isolation of mRNA herein capitalizes on the presence of a poly A tail at the 3' end of the mRNA. The 3' tail is utilized to separate the mRNA from the other RNA species. Separation is achieved by chromatography on an oligo dT cellulose column by binding of the poly A tail of mRNA with the T residues on the cellulose column. The unbound RNA can be washed free of the column and the mRNA can be eluted by buffers that destabilize the A-T duplex. The RNA concentration is then determined spectrophotometrically.

The integrity of the mRNA preparation, i.e., whether it is full-length or simply a small fragment with a 3' poly. A tail, is determined by in vitro translation of the mRNA. A full-length mRNA can be selected and used to construct a cDNA library. The rubber polymerase gene in this library can be detected utilizing either nucleic acid probes or antibodies if the cDNA library expresses the cDNA.

The plant materials that are used for the isolation of mRNA can be from any plant or organisms that are capable of synthesizing rubber. For example, since Hevea seedlings produce rubber from the very earliest stages of growth, mRNA capable of encoding rubber polymerase can be obtained from Hevea seedlings. The isolated mRNA is then used as a template for synthesis of first-strand cDNA molecules. The first-strand cDNA is, in turn, used as a template in a second-strand DNA synthesis utilizing, e.g., DNA polymerase I. In this manner, a cDNA library can be generated.

To find the nucleotide sequence in the cDNA library that is capable of encoding rubber polymerase, a complementary nucleic acid probe can be used that contains a predicted nucleotide sequence based upon a known amino acid sequence of the rubber polymerase enzyme. In the alternative, polyclonal or monoclonal antibodies to rubber polymerase can be produced in experimental animals or in hybridomas, respectively, and used to identify those transformed host cells that produce rubber polymerase.

In a preferred embodiment of the present invention, at least a portion of the amino acid sequence of the purified rubber polymerase enzyme is determined by sequencing. Nucleic acid probes based upon the predicted nucleotide sequences can be constructed in accordance with conventional laboratory techniques. In formulating the sequences to be constructed, different strategies can be adopted.

Where nucleotides are ambiguous at a number of locations, the ambiguity can be circumvented by synthesizing mixtures of nucleotides that represent every codon combination. Where codon ambiguity is excessive, however, alternative strategies have to be used. In one embodiment of the present invention, groups of mixed oligonucleotides can be synthesized where the ambiguity is held to a minimum within each group and the combination of sequences among the groups represent all possible coding combinations. For example, a collection of short nucleic acid sequences can be made, each sequence containing about 15 to 20 bp and representing every possible codon combination. In another embodiment of the present invention, long nucleic acid sequences, e.g., ones that have about 30 to about 60 bp with minimal mismatch base pairs, can also be designed. The synthesis of these nucleotides are exemplified in, e.g., Suggs et al., *Proc. Natl. Acad. Sci.*, 78: 6613-6617 (1981), Ullrich et al., *EMBO J.*, 3: 361-364 (1984), Shah et al., *Science*, 233: 478-481 (1986), and Lathe R., *J. Mol. Biol.*, 183: 1-12 (1985), Ohtsuka et al., *J Biol. Chem.* 260: 2605-2608 (1985), Martin & Castro, *Nucleic Acid Res.* 13: 8927-8938 (1985), the contents of each of which are incorporated herein by reference.

In as yet another embodiment of the present invention, probes can be designed using base analogs at ambiguous codon positions that form base pairs with the natural bases without destabilizing duplex formation In particular, 2-deoxyinosine can be used since it can form a base pair at A/C or G/T ambiguities and the instability produced is not large enough to cause problems with duplex formation.

Alternatively, a base analog with an increased hybridization potential, e.g., 2-amino-2-deoxyadenosine, can be substituted for a normal base within a probe. This 2-amino-2-deoxyadenosine can pair with T residues and form three hydrogen bonds instead of the normal two hydrogen bonds. This bonding results in additional duplex stability compensating for the disruptive effects of ambiguity at the degenerative positions in codons. Incorporating two or more of these methods is also a viable approach to generating a probe. The end result of any combination of these techniques would be a nucleic acid sequence specific for the gene of interest.

A nucleic acid probe for the detection of the rubber polymerase gene can be modified to detect extremely small amounts of the gene, e.g., by labeling the probe with [$^{32}$P]-phosphate at the 3' or 5' end, or with biotin moieties by a variety of conventional techniques as in, e.g., Rigby et al., *J. Mol. Biol.*, 113: 237-251 (1977), Murasugi et al., DNA. 3: 269-277 (1984), and Haas et al., *Nucleic Acid Res.*, 14: 3976 (1986), the contents of each of which are incorporated herein by reference. The radioactive labeling can be performed using commercially available 3' or 5' end labeling kits from, e.g., Amersham Corporation (Arlington Heights, Ill.) or New England Nuclear (Boston, Mass.), and following the manufacturer's directions. The rubber polymerase gene in the DNA libraries can then be identified by hybridization with the labeled probe.

Gene libraries expressing the rubber polymerase gene can also be screened with antibodies to the rubber polymerase enzyme. Whether the screening is done by nucleic acid probes or with antibodies, the goal of such screening is to detect a positive hybridization or reaction signal, respectively, and to sequentially enrich for the clone that produces the positive signal.

In another embodiment of the present invention, a recombinant lambda Phage containing Hevea cDNA library is screened substantially according to the method of Maniatis et al., loc. cit., using [$^{32}$P]-labelled rubber polymerase specific oligonucleotide. Hybridization is carried out at 30° C. to 33° C. for 16 to 24 hours, after which the filters are washed at either 37° C., 40° C. or 42° C. The membranes are autoradiographed to identify the hybrid vectors that carry the rubber polymerase gene.

An isolated DNA fragment that has been identified as carrying the rubber polymerase gene by hybridization with a rubber polymerase gene specific probe, e.g., a seventeen base probe, can be tested with a second rubber polymerase gene specific probe, e.g., a fifty-three base oligonucleotide. A positive reaction between both of the rubber polymerase gene specific probes and the isolated rubber polymerase DNA sequence serves to confirm the identity of the rubber polymerase gene.

DNA from the clone that carries a rubber polymerase gene and that reacts positively with the rubber polymerase gene specific probe can be isolate and the rubber polymerase gene removed and ligated to another vector. Removal of the rubber polymerase gene is accomplished by digesting the DNA from the original positive clone with an enzyme, e.g., EcoRI, that frees the Hevea cDNA from the vector DNA. This method of gene removal is feasible because when the Hevea cDNA library is constructed, the cDNA is inserted into the lambda gt11 phage vector at an EcoRI restriction site. Digestion of the phage that contains the cDNA insert with EcoRI, therefore, frees the insert from the viral vector sequences.

The rubber polymerase gene isolated in the above-described manner can be subcloned into another plasmid for production of large quantities of this gene. In one embodiment of the present invention, the gene can be subcloned in plasmid pBR322 and maintained in *E. coli*. The *E. coli* cells containing the pBR322 plasmid with the rubber polymerase qene are propagated to produce large quantities of the rubber polymerase DNA sequence. This DNA can be extracted from the transformed hosts in accordance with conventional laboratory techniques.

A restriction map of the rubber polymerase DNA sequence can be constructed by treating the DNA sequence with restriction enzymes, e.g., AccI, AvaI, BamHI, BclI, BglII, EcoRI, HincII, HindIII, HinoI, KonI, PstI, PvuII, SalI, Sau3A, ScaI, SmaI, SphI, SstI, SstII, StuI, TaoI, XbaI and XhoI, and determining the size of the DNA fragments generated therefrom. Based upon the identity of the restriction enzymes that are capable of digesting the rubber polymerase DNA sequence and the size of the DNA fragments each of these enzymes generates, a restriction map of the rubber polymerase DNA sequence can be generated.

The following example is given by way of illustration to facilitate a better understanding of the present invention and are not intended to limit the scope thereof.

EXAMPLE 1

Isolation of DNA from Plant and Other Organisms

The fungus, *Lactarius corrugis* was grown on a medium containing 2.5% (w/v) malt and 1% neopeptone for about two weeks, harvested by vacuum filtration and washed with distilled water.

Leaves from *Hevea brasiliensis* and guayule plants were harvested from plants grown in the greenhouse. The leaves were surface-sterilized by immersion in 5% chlorox solution for 15 minutes and rinsed in distilled water and air dried. Guayule shoot from tissue culture previously frozen at −20° C. for 6 months was used directly for DNA isolation.

About 0.5 to about 0.75 g of plant materials were frozen quickly in liquid nitrogen and ground to a fine powder with a mortar and pestle. While still frozen, the fine powder was transferred to a 30 ml centrifuge tube After the liquid nitrogen was allowed to evaporate from the powder, 15 ml of a solution containing 100 mM Tris at pH 8.0, 50 mM EDTA, 500 mM NaCl, 10 mM mercaptoethanol, and 1 ml of 20% SDS were added to the tube. The mixture was incubated at 65° C. for 10 minutes Then 5 ml of 5 M potassium acetate was added and the contents of the tube were mixed thoroughly. The tube and contents were placed at 0° C. for 20 minutes and centrifuged at 15,000 rpm in a SS34 rotor at 4° C. for 20 minutes.

After centrifugation, the supernatant fluid was poured through a 60 μmesh filter into a clean tube containing 10 ml isopropanol and then kept at −20° C. for 30 minutes DNA present in the filtrate was pelleted by centrifugation at 12,000 rpm in a SS34 rotor at 4° C. for 15 minutes. The pellet was allowed to dry at room temperature for 30 minutes and was then resuspended in 0.7 ml of a solution containing 50 mM Tris, 10 mM EDTA at pH 8.0, and 75 μl of a 3 M sodium acetate solution. About 500 μl of isopropanol was added to reprecipitate the dissolved DNA. The precipitated DNA was pelleted in a microfuge for 2 minutes and resuspended in 100 μl of a buffer containing 10 mM Tris, and 1 mM EDTA at pH 8.0 (hereafter "1×TE buffer"). The resuspended DNA was banded at 45,000 rpm in a Ti 70 rotor at 20° C. for 68 hours in a cesium chloride gradient containing 0.95 g cesium chloride and 250 μg of ethidium bromide per ml of DNA solution.

The fluorescent ethidium bromide band was removed from the centrifuge tube by side puncture and the gradient was extracted with isopropanol to remove ethidium bromide DNA was harvested from the gradient, diluted two-fold with distilled water and precipitated by the addition of 2.5 volumes of cold 95% ethanol. The precipitated DNA was recovered by centrifugation, after which it was resuspended in 1×TE buffer and analyzed by gel electrophoresis, e.g., according to Maniatis et al., loc. cit.

The concentration of the DNA isolated in this manner was estimated spectrophotometrically. The molecular weight of the DNA was determined by gel electrophoresis and found to be greater than or equal to 23 kb.

EXAMPLE 2

Isolation of mRNA From Hevea Plants

Two to four month old Hevea seedlings grown in a greenhouse and weighing about 15 g were cut at soil level and placed on ice. The plants were cut into small pieces, then frozen in liquid nitrogen and ground in a mortar and pestle to a fine powder. The stem sections required vigorous grinding to reduce to a fine powder. The grounded material was transferred to a chilled blender to which was added 100 ml of ice cold buffer containing 4.5 M guanidinium isothiocyanate, 25 mM sodium citrate at pH 7.0, 50 mM EDTA, 0.1 M mercaptoethanol and 2% laurylsarcosine. The suspension was blended at 4° C. for six 30 second bursts with cooling between bursts and centrifuged at 0° C. for 10 minutes at 8,000×g. The supernatant fraction was collected. The pellet was re-extracted with 100 ml of the same buffer and the mixture was centrifuged as before. The supernatant fractions were combined and centrifuged again to remove additional debris. RNA was precipitated from the supernatant at −20° C. for 12 hours by the addition of 0.04 volume of a solution containing 4.5 M sodium acetate at about pH 5.5 and 0.7 volume of absolute ethanol The pellet was collected by centrifugation at 8,000×g for 10 minutes at 0° C. and resuspended in 15 ml of 4.5 M guanidinium isothiocyanate, 25 mM sodium citrate at pH 7.0, 10 mM dithiothreitol, 20 mM EDTA and 1% laurylsarcosine. The solution was precipitated as before and the pellet was collected by centrifugation. The resuspension and precipitation processes were repeated twice more and the final pellet was washed with absolute ethanol four times. The total RNA isolated was chromatographed on oligo dT cellulose, e.g as in Maniatis et al., loc. cit. In a preferred embodiment, the procedure was carried out batchwise instead of in a column.

The oligo dT cellulose, in about 2.5 ml swelled volume, was equilibrated overnight at room temperature with a binding buffer containing 25 mM sodium citrate at pH 7, 0.5 M NaCl, 1 mM EDTA, and 0.1% SDS. All glassware and solutions were previously treated with 0.1% diethylpyrocarbonate and sterilized. All procedures were performed at room temperature with the operator wearing surgical rubber gloves to minimize nuclease contamination of the mRNA preparation.

The total RNA was suspended in 10 ml of water and heated at 65° C. for 5 minutes. After quick cooling on ice, 1 volume of a 2-fold concentrate ("2×") of the binding buffer was added to the RNA and the mixture was incubated batchwise with the oligo dT cellulose for 30 minutes with slow end-over-end rotation. The oligo dT was separated from the solution by centrifugation at 1500 rpm in a RT6000 centrifuge for 3 minutes. The RNA was decanted from the cellulose and heated at 65° C. for 5 minutes and reincubated with the cellulose for 20 minutes. The oligo dT cellulose was first washed with 10 ml of binding buffer followed by 10 ml of a solution containing 25 mM sodium citrate at pH 7, 0.1 M NaCl, 1 mM EDTA and 0.1% SDS, for 20 minutes per wash.

The mRNA was eluted from the oligo dT cellulose three times with 2 ml of a solution containing 25 mM sodium citrate at pH 7, 1 mM EDTA, 0.05% SDS and eluted once with 5 ml of water at 48° C. The mRNA-containing fractions were combined and potassium acetate was added to 0.3 M. The mRNA was then precipitated with 2.5 volumes of absolute ethanol for 12 hours at −20° C. and resuspended in 1.5 ml water, divided into aliquots and stored at −80° C. The RNA concentration was determined spectrophotometrically at 260 nm. The Hevea mRNA isolated represented 1% of the total RNA population.

EXAMPLE 3

Synthesis and Cloning of cDNA From Hevea mRNA

A first strand cDNA of Hevea was synthesized in vitro from mRNA with the use of reverse transcriptase. The reagents for the synthesis of cDNA used herein were purchased as a kit from New England Nuclear (Boston, Mass.). Reactions were performed substantially in accordance with the supplier's instructions. In particular, for a first strand cDNA synthesis, the reaction mixtures were scaled up to 100 µl volumes in 5 tubes, each containing 20 µl reverse transcriptase reaction buffer, 5 µl of 600 mM β-mercaptoethanol, 5 µl of RNaseA inhibitor containing 20 U of activity, 10 µg of oligo(dT)12-18 in 10 µl, 10 µl of a mixture containing 2.5 mM dCTP, 5 mM each of dGTP, dATP and dTTP, 100 Ci/10 µl of [$^{32}$P]-dCTP having a specific activity of 800 Ci/mmol, 1 µg of Hevea poly A mRNA in 35 µl and 5 µl of reverse transcriptase, containing 50 U of activity.

The reaction mixture was incubated at 42° C. for 1 hour. The contents of the five tubes were pooled and boiled for 3 minutes to heat-denature the mRNA-cDNA hybrid The tubes were then incubated on ice for 5 minutes and the denatured proteins were removed by centrifugation.

A second strand cDNA was synthesized based upon the first strand cDNA. For the second strand synthesis, 98 µl from the first strand synthesis reaction mixture was placed in each of five tubes. To each tube were added 12 µl of water, 45 µl of DNA polymerase I buffer, 10 µl of a mixture containing 2.5 mM dCTP 5 mM each of dGTP dATP and dTTP 10 µl [$^{32}$P]-dCTP containing 100 µCi and a specific activity of 800 Ci mmol and 15 µl of DNA polymerase I that had 120 U of activity. The tubes were incubated at 15° C. for 2 hours.

The hairpin loop generated by reverse transcriptase was hydrolyzed by S1 nuclease digestion by the addition of 5 µl of water, 50 µl of S1 reaction buffer and 5 µl of S1 nuclease containing 50 U of activity to each tube and incubating at 37° C. for 30 minutes. Following the S1 nuclease digestion, the samples were pooled and the cDNA duplexes were extracted with phenol:-chloroform in a 1:1 ratio. The aqueous phase was extracted twice with ether and the DNA was precipitated with 95% ethanol. The precipitate was resuspended in 1 ml of 1×TE buffer. The resulting solution was concentrated to 50 µl with an Amicon ultrafiltration device (Centricon) that had a molecular weight cut off of 30,000 dalton.

The cDNA duplexes obtained were methylated by EcoRI methylase Methylation was performed in a 65 μl volume containing 50 μl cDNA, 6 μl of 0.086 mM S-adenosylmethionine 6 μl of a mixture containing 1 M NaCl, 1 M Tris HCl 10 mM EDTA at pH 8 0, and 3 μl EcoRI methylase that has an activity of 60 U. The reaction was performed at 37° C. for 2 hours followed by incubation at 65° C. for 20 minutes.

EcoRI linkers were ligated to the methylated cDNA duplexes Fifty microgram of the EcoRI linkers were dissolved in 50 μl 1×TE buffer at 65° C. for 2 minutes. Five microliters of the linkers were added to 65 μl of the methylated cDNA followed by addition of 8 μl of 10 mM ATP at pH 7.5, 8 μl of a mixture containing 660 mM Tris at pH 7.6, 66 mM MgCl2, 100 mM dithiothreit 1 and 5 μl of T4 DNA ligase that had an activity of 5 U. This mixture was incubated at 12° C. for 20 hours after which 3 μl of ATP and DNA ligase were added Incubation was continued for 10 hours. The linkered methylated cDNA was restricted with EcoRI and the enzyme was heat-inactivated at 65° C. for 20 minutes. The sample was diluted with 1 ml of 1×TE buffer and the unassociated EcoRI linkers were removed by concentration through a Centricon device that had a molecular weight cutoff of about 30,000 daltons.

The linkered methylated cDNA duplexes were ligated to a vector as follows: About 100 ng of the cDNA duplexes was added to 10 μg of EcoRI digested and phosphatase-treated lambda gt11 DNA (Promega Biotec, Madison, WI) and precipitated with ethanol. DNA from the hybrid vector was resuspended in 20 μl of 1×TE buffer and ligation with the cDNA was performed as before. These lambda gt11 hybrids were packaged, amplified and quantitated.

EXAMPLE 4

Formulation of a Nucleic Acid Probe for the Identification of Hevea Rubber Polymerase Gene Purified Hevea rubber polymerase enzyme was submitted to the University of Michigan, Protein Sequencing Facility (Ann Arbor, Mich.) for amino acid sequencing. Table 1 shows the results of the sequencing effort from four different regions of the purified enzyme. The numbers above the amino acid sequences represent the amino acid position within the respective peptide. The sequences are shown left to right from the N terminus.

TABLE 1

Amino Acid Sequences of Hevea Rubber Polymerase

N Terminal Enzyme Sequence
```
1               5              10
leu—thr—gln—gly—lys—lys—ile—thr—val—leu—ser—ile—
          15
—asp—gly—gly
```

Fragment 4

TABLE 1-continued

Amino Acid Sequences of Hevea Rubber Polymerase
```
1               5              10
val—asp—phe—his—leu—ser—ala—leu—phe—lys—ser—
          15                    20
—leu—asp—cys—glu—asp—tyr—tyr—leu—arg—ile
```

Fragment 5
```
1               5
val—asp—phe—his—leu—ser—ala
```

Fragment 7
```
1               5              10
tyr—glu—ala—lys—asp—ile—lys—asp—phe—tyr—leu—glu—
          15                    20
—asn—cys—pro—lys—ile—phe—pro—lys—glu—(ser)—arg—
          25
—asp—asn—tyr—(asp)—(pro)—ile
```

Table 2 shows the least ambiguous amino acid sequence for the formulation of a 17 bp nucleic acid probe specific for the Hevea rubber polymerase gene. The nucleic acid probe was deduced from amino acid residues 13 to 18 of peptide fragment 4 of Table 1. Each amino acid of this sequence has two possible codons

TABLE 2

Nucleotide Sequences Deduced From Amino Acid Residues 13 to 18 of Peptide Fragment 4

| Amino Acid N-terminus | asp—cys—glu—asp—tyr—tyr |
|---|---|
| PROBE | 5' GAT TGT GAA GAT TAT TA 3'<br>C   C   G   C   C |

The probe is written in the conventional 5'→3' direction and consisted of a mixture of thirty-two nucleotide sequences, each being 17 bp in length, and one of which would exactly complement the Hevea rubber polymerase gene.

The formulation of a longer probe follows the same principle as above, with mismatched base pairs being placed at positions within the DNA sequence that do not interrupt long stretches of homology. Additionally, in regions of homology, deoxyinosine (dI) residues were placed at the degenerate nucleotide positions. The longer probe shown in Table 3 was deduced from amino acid residues 1 to 19 of peptide fragment 7 of Table 1. The probe is 53 bp in length, 32-fold degenerate and contains eight possible mismatches and five dI residues.

The 5' end of the probe contained a 17 bp homology interrupted with three dI residues. The 3' end of the probe contained a 15 bp homology interrupted with two dI residues. At the wobble positions within the probe, A or T residues were chosen when applicable because the gene as represented by the amino acid sequence was predominantly A-T rich.

A 17 bp and a 53 bp probe as described above, each specific for Hevea rubber polymerase gene, were synthesized by Pharmacia (Milwaukee, Wis.).

TABLE 3

Nucleotide Sequences Deduced From Amino Acid Residues 1 to 19 of Peptide Fragment 7

| Amino Acid N Terminus | 1               5              10<br>tyr—glu—ala—lys—asp—ile—lys—asp—phe—tyr<br>          15<br>leu—glu—asn—cys—pro—lys—ile—phe—pro |
|---|---|

TABLE 3-continued

Nucleotide Sequences Deduced From Amino Acid Residues 1 to 19 of Peptide Fragment 7

| PROBE | 5' | TAT | GAA | GCI | AAA | GAI | ATI | AAA | GAT | TTT | TAT |
|---|---|---|---|---|---|---|---|---|---|---|---|
| | | C | | G | | G | | | | | |
| | | TTA | GAA | AAT | TGT | CCI | AAA | ATI | TT | 3' | |
| | | | | | C | | G | | | | |

EXAMPLE 5

The Identification of a Hybrid Vector That Carries a Rubber Polymerase Gene

A 17 base Hevea rubber polymerase gene specific oligonucleotide produced as above was labeled with [$^{32}$P]-phosphate and utilized as a probe to identify a rubber polymerase DNA sequence in a Hevea cDNA library in recombinant lambda gt11 phages. An unamplified Hevea cDNA library containing $4 \times 10^5$ phages, of which 46% contained Hevea cDNA, was used for screening in accordance with Maniatis et al., loc. cit., with some modifications, as described below.

Ten thousand lambda gt11 phages were plated on each of forty 100 mm petri plates on a lawn of *E. coli*. Of this number, approximately 4600 phages per plate were estimated to contain Hevea cDNA. The hybrid phage DNA was isolated, bound to Plaque Screen nylon membranes (Dupont, Boston, Mass.) and prehybridized for about 16 to 24 hours at 30° C. to 35° C. in 40 ml of the hybridization solution. The hybridization solution contained 20 ml of 1% (w/v) polyvinylpyrrolidone 360, ficoll 400 and bovine serum albumin, 5 ml of 1 M Tris at pH 7.5, 33.3 ml of 3 M NaCl, 10 ml of 1% (w/v) sodium pyrophosphate, 10 ml of 1% (w/v) SDS, 1 ml of 10 mg/ml salmon sperm DNA, sheared and heat denatured, and 19.7 ml of water.

After hybridization, the hybridization solution was removed and replaced with 10 ml of the same but without the salmon sperm DNA and with about 106 to 107 dpm of [$^{32}$P]-phosphate labeled oligonucleotide that had a specific activity of 2 to $8 \times 10^8$ dpm/μg. The hybridization cocktail containing the labeled probe was heated at 80° C. for 5 minutes and was then added to the Plaque Screen nylon membranes containing the recombinant phage DNA Hybridization was performed at 30° C. to 33° C. for 16 to 24 hours. The nylon membranes were washed at 37° C., 40° C. or 42° C. with 1 liter of 6×SSC containing 0.25% SDS and then 1.5 liter of 6×SSC and autoradiographed. A 1×SSC solution contained 0.15 M NaCl and 0.015 M trisodium citrate. The area around a positive plaque was picked and re-screened until a single positive plaque could be isolated.

EXAMPLE 6

The Isolation of a DNA Fragment that Reacts with the Rubber Polymerase Gene Specific Probe Hybrid phages that contained Hevea DNA were propagated and the DNA isolated therefrom. The host cell, *E. coli* NM538, was cultured overnight at room temperature. Twenty ml of this bacterial culture was mixed with 2 ml of a phage suspension, at 108 phages/ml, and incubated at 37° C. for 20 minutes After incubation, the mixture was added to a 500 ml flask containing 250 ml of a medium containing in per liter of water, 10 g casamino acid, 5 g of yeast extract, 3 g of NaCl, 2 g of KCl, 2 g of MgCl2.6H20, at pH 7.5. The flask was shaken at 200 rpm for 16 hours at 37° C. Lysis of bacterial cell was demonstrated by the appearance of cell debris in the growth medium. One ml of chloroform was added to the flask and incubation was continued, with shaking, for 15 minutes at 37° C. Sodium chloride was subsequently added to the mixture in the flask to a final concentration of 0.5 M and the entire mixture was incubated for an additional 15 minutes. After incubation, cell debris was removed by centrifugation at 7000 rpm in a GSA rotor for 15 minutes at 4° C. Solid polyethylene glycol 8000 ("PEG") was added to the clear supernatant fluid to a concentration of 10% (w/v). The phages were precipitated from the supernatant by overnight incubation at 4° C.

The precipitated phages were concentrated by centrifugation at 7000 rpm in a GSA rotor for 15 minutes at 4° C. The pellet was resuspended in a buffer containing 10 ml of 50 mM Tris, at pH 7.4, and 10 mM MgSO4 (hereafter "TM buffer"). PEG was removed from the phage suspension by extraction with an equal volume of chloroform, e.g., by shaking the mixture containing PEG and phages in a small screw top test tube. The aqueous phase was separated from the organic phase by centrifugation at low rpm at room temperature.

The phages were further purified by centrifugation through glycerol gradients. The gradients were constructed by pipetting 3 ml of TM buffer containing 40% (v/v) glycerol into a 12 ml centrifuge tube and overlaying this solution with 4 ml to 5% (v/v) glycerol. The phage suspension, about 4 to 5 ml, was added to the top of the gradient and the tubes were centrifuged in as SW41 rotor at 35,000 rpm for 1 hour at 4° C.

The phages sedimenting at the bottom of the tube were resuspended in 1 ml of TM buffer and treated with 20 μl of 10 mg/ml DNaseI and 10 μl of a 20 mg/ml solution of RNaseA for 30 minutes at 37° C. One hundred microliter of a buffer containing 50 mM Tris at pH 8.0 and 100 mM EDTA, and 50 μl of 10 mg/ml pronase were added to the phages and the mixture was incubated at 37° C. for 15 minutes. Twenty microliters of 10% SDS was then added and the entire mixture incubated for 30 minutes at 37° C. The DNA preparation was thereafter extracted with phenol, then chloroform, precipitated in ethanol twice and resuspended in 1×TE buffer.

EXAMPLE 7

Subcloning of the Hevea Rubber Polymerase DNA Sequence

The subcloning procedure involved excising the rubber polymerase DNA sequence from the lambda gt11 hybrid phages containing the rubber polymerase DNA sequence, i.e., lambda RPc1, and inserting the rubber polymerase DNA sequence into plasmid pBR322 previously digested with EcoRI, to produce a hybrid plasmid, pRPc1. The pRPc1 plasmid was transferred into *E. coli* HB101, thereby producing a transformed E. coli, ATCC No. 68055.

More specifically, 20 μl containing 2.8 μg of EcoRI-digested recombinant lambda phage containing the rubber polymerase gene was mixed with 15 μl, containing about 1.5 μg, of EcoRI-digested and dephosphorylated pBR322, 10 μl of water and 3 μl of DNA ligase. The ligation reaction was performed at 12° C. for 24 hours and the reaction products were analyzed by agarose gel electrophoresis. The ligation reaction mixture was diluted to 100 μl with 1×TE buffer and used to transform competent *E. coli* HB101 cells, in accordance with the directions provided by the manufacturer of commercially available subcloning kits, e.g., Bethesda Research Laboratories (Gaithersburg, MD).

The transformed cells were screened for the presence of both the pBR322 and RPc1 sequences by restriction digestion with EcoRI. The appropriate transformed cell produced two DNA fragments upon digestion with EcoRI a 4.3 kb fragment representing the pBR322 vector and a 1.9 kb fragment representing RPc1.

Hundreds of transformed cells were produced of these, sixteen were picked at random and analyzed for the presence of the approximately 1.9 kb rubber polymerase gene insert. The sixteen transformed cells were individually inoculated into 2.5 ml of L-broth containing 50 μg/ml of ampicillin and grown overnight at 37° C. One ml of the cells was sedimented by centrifugation in a microfuge tube and resuspended in 100 μl of 2 mg/ml lysozyme in 50 mM glucose, 10 mM EDTA 25 mM Tris at pH 8.0, and placed on ice for 30 minutes Two hundred μl of 0.2 N NaOH containing 1% SDS was added to the mixture, the mixture was gently vortexed and placed on ice for 5 minutes About 150 μl of 3 M sodium acetate at pH 4.8 was subsequently added and the mixture was again placed on ice for 20 minutes to precipitate the protein, chromosomal DNA and high molecular weight RNA. The precipitated materials were centrifuged for 5 minutes and the supernatant fluid was poured into a new microcentrifuge tube. Plasmid DNA was precipitated from the supernatant fluid by adding 1 ml of 95% ethanol and freezing at −20° C. for 30 minutes.

The insoluble nucleic acid was collected by centrifugation, resuspended in 100 μl of a mixture containing 0.1 M sodium acetate and 50 mM Tris at pH 8.,0, and reprecipitated with two volumes of 95% ethanol. The process of centrifugation, resuspension and reprecipitation was repeated twice and the pellet was finally resuspended in 50 μl of 1×TE buffer Ten μl of the isolated DNA was digested with EcoRI and analyzed by gel electrophoresis. An individual recombinant plasmid was chosen that possessed the 1.9 kb insert and the plasmid DNA was isolated from the transformed cells carrying this recombinant plasmid

EXAMPLE 8

Restriction Mapping of the Rubber Polymerase Gene

Restriction mapping of the DNA sequence containing the rubber polymerase gene was performed by incubating the DNA sequence separately with each of the following enzymes: AccI ("A"), AvaI, BamHI ("B"), BclI, BglII ("BII"), EcoRI ("E"), HincII, HindIII ("H"), HinpI ("HI"), KonI, PstI, PvuII, SalI, Sau3A, ScaI, SmaI, SphI, SstI, SstII, StuI, TaoI ("T"), XbaI ("X") and XhoI ("XI"). These enzymes were purchased from Bethesda Research Laboratories (Gaithersburg, Md.) or New England Biolab (Beverly, Mass.) and used according to the manufacturer's directions. A restriction map of RPc1 is shown in FIG. 1.

In FIG. 1, the numbers in parentheses represent the size of the restriction fragments produced by each restriction endonuclease. The ends of the DNA sequence containing the rubber polymerase gene are defined by the enzyme EcoRI. The restriction enzymes AccI, BglII, XbaI, HinpI, TagI and Sau3A were found to digest the rubber polymerase DNA. The enzymes tested but not shown in FIG. 1 were found not to digest RPc1.

AccI and BglII each digests the DNA within 50 base pairs of opposite ends of the gene with a single XbaI site located approximately 200 base pairs from the BglII site. The enzyme HinpI was found to have at least one site within the gene but the restriction fragment pattern was ambiguous and the site could only be narrowed to two locations, hence the question mark designation in FIG. 1. This HinpI site was found to lie about 650 base pairs from the one end of the gene. The enzyme TagI digested the gene in at least two sites but the restriction fragment pattern only allowed an approximation of these sites. Sau3A digested the DNA a number of times and produced too complex a restriction pattern to accurately interpret the results.

EXAMPLE 9

Reaction Between A 53 Base Rubber Polymerase Gene Specific Oligonucleotide and Isolated Polymerase Gene Rubber A fifty-three base rubber polymerase gene specific probe, based upon the probe sequence of Table 3, was produced. This probe was labeled with [$^{32}$P]-phosphate and hybridized at 32° C. with RPc1 DNA, pRPc1 that had been digested with EcoRI to produce pBR322 and RPc1, and with pBR322 alone digested with EcoRI. After hybridization, the DNA fragments were washed at 40° C., 45° C., 50° C. and 60° C.

At 40° C., the probe was found to bind to all DNA tested, with the greatest affinity for the RPc1 fragment. As the wash temperature was increased to 50° C., a temperature approaching the $T_m$ of the probe, the binding of the probe became very specific. No signal was observed for a DNA molecule other than RPc1. At 60° C., above the Tm of the probe, no signal was evident.

What is claimed is:

1. A DNA fragment that comprises a first DNA sequence that encodes rubber polymerase or a fragment thereof.

2. A DNA fragment as claimed in claim 1, wherein said fragment further comprises a second DNA sequence that is capable of influencing the expression of the first DNA sequence.

3. A DNA fragment as claimed in claim 1, wherein said first DNA sequence is capable of encoding an N-terminal amino acid sequence leu-thr-gln-gly-lys-lys-ile-thr-val-leu
ser-ile-asp-gly-gly.

4. A DNA fragment as claimed in claim 1, wherein said first DNA sequence is capable of encoding an amino acid sequence val—asp—phe—his—leu—ser—ala—leu—phe—lys—ser—leu—

—asp—cys—glu—asp—tyr—tyr—leu—arg—ile.

5. A DNA fragment as claimed in claim 1, wherein said first DNA sequence is capable of encoding an amino acid sequence tyr—glu—ala—lys—asp—ile—lys—asp—phe—tyr—leu—glu—

—asn—cys—pro—lys—ile—phe—pro—lys—glu—X—arg—asp—

—asn—tyr—X—X—ile, wherein X is an amino acid.

6. A DNA fragment as claimed in claim 1, wherein said DNA sequence comprises a restriction site for each of the enzymes EcoRI, AccI, TagI, Sau3A, HinoI, XbaI and BglII and free of restriction sites for the enzymes AvaI, BamHI, BclI, HincII, HindIII, KpnI, PstI, PvuII, SalI, ScaI, SmaI, SohI, SstI, SstII, StuI and XhoI.

7. A DNA fragment as claimed in claim 1, wherein the DNA sequence is encoded substantially by a sequence contained in E. coli strain, ATCC no. 68055.

8. A DNA fragment as claimed in claim 2, wherein said second DNA sequence comprises a promoter.

9. A DNA fragment as claimed in claim 8, wherein said promoter is selected from the group consisting of a bacterial promoter, a plant promoter and a virus promoter.

10. A DNA fragment as claimed in claim 9, wherein said promoter is a bacterial promoter and is either a trp promoter or a tac promoter.

11. A DNA fragment as claimed in claim 9, wherein said promoter is a plant promoter and is Pnos.

12. A DNA fragment as claimed in claim 9, wherein said promoter is a virus promoter.

13. A DNA fragment as claimed in claim 12, wherein said virus promoter is a cauliflower mosaic virus promoter.

14. A hybrid vector comprising a DNA fragment as claimed in claim 1, wherein said vector is capable of being transferred to and replicating in a host.

15. A hybrid vector as claimed in claim 14, wherein said vector is plasmid pRPc1.

16. A transformed host comprising the hybrid vector as claimed in claim 14, wherein said host is capable of expressing the DNA fragment.

17. A transformed host comprising the DNA fragment as claimed in claim 1, wherein said host is capable of expressing the DNA fragment.

18. A transformed host as claimed in claim 16, wherein said host is selected from a group consisting of a plant, a bacterium and a fungus.

19. A transformed host as claimed in claim 18, wherein said host is a fungus.

20. A transformed host as claimed in claim 19, wherein said fungus is selected from the group consisting of a Lactarius species, and an Aspergillus species.

21. A transformed host as claimed in claim 18, wherein said host is a plant.

22. A transformed host as claimed in claim 21, wherein said plant is selected from the group consisting of a Hevea species and guayule.

23. A transformed host as claimed in claim 21, wherein said plant is selected from the group consisting of a tobacco species, a grass species and a perennial plant species.

24. A transformed host as claimed in claim 18, wherein said host is a bacterium.

25. A transformed host as claimed in claim 24, wherein said bacterium is selected from the group consisting of an E. coli strain, a Bacillus species, and an Aorobacterium species.

26. A process for the production of rubber in vitro comprising the steps of
providing a DNA fragment as claimed in claim 1,
transferring said DNA fragment to a host cell to produce a transformed host cell and
culturing said transformed host in a suitable medium for the production of rubber polymerase using said rubber polymerase to catalyse the synthesis of rubber in vitro.

27. A process for the production of rubber in vivo comprising the steps of
providing a DNA fragment as claimed in claim 1,
transferring said DNA fragment to a host cell to produce a transformed host cell and
culturing said transformed host in an environment that is suitable for the production of rubber in vivo.

* * * * *